United States Patent
Nishida et al.

(10) Patent No.: US 11,839,697 B2
(45) Date of Patent: Dec. 12, 2023

(54) CORNEAL ENDOTHELIAL CELL MARKER AND USE THEREOF

(71) Applicant: Osaka University, Osaka (JP)

(72) Inventors: Kohji Nishida, Osaka (JP); Motokazu Tsujikawa, Osaka (JP); Susumu Hara, Osaka (JP); Satoshi Kawasaki, Osaka (JP); Masahito Yoshihara, Saitama (JP); Masayoshi Itoh, Saitama (JP); Hideya Kawaji, Saitama (JP)

(73) Assignee: OSAKA UNIVERSITY, Osaka (JP)

( * ) Notice: Subject to any disclaimer, the term of this patent is extended or adjusted under 35 U.S.C. 154(b) by 943 days.

(21) Appl. No.: 16/621,528

(22) PCT Filed: Jun. 19, 2018

(86) PCT No.: PCT/JP2018/023185
§ 371 (c)(1),
(2) Date: Dec. 11, 2019

(87) PCT Pub. No.: WO2018/235786
PCT Pub. Date: Dec. 27, 2018

(65) Prior Publication Data
US 2020/0101200 A1 Apr. 2, 2020

(30) Foreign Application Priority Data
Jun. 19, 2017 (JP) ................. 2017-119518

(51) Int. Cl.
*A61L 27/38* (2006.01)
*C12Q 1/06* (2006.01)
(Continued)

(52) U.S. Cl.
CPC .......... *A61L 27/3808* (2013.01); *A61K 35/30* (2013.01); *A61K 35/545* (2013.01);
(Continued)

(58) Field of Classification Search
None
See application file for complete search history.

(56) References Cited

U.S. PATENT DOCUMENTS

| 2009/0232772 A1 | 9/2009 | Amano et al. |
| 2015/0202256 A1 | 7/2015 | Nakamura et al. |
(Continued)

FOREIGN PATENT DOCUMENTS

| CN | 106167790 A | 11/2016 |
| EP | 2894218 A1 | 7/2015 |
(Continued)

OTHER PUBLICATIONS

Zhang et al. Isolation and Transplantation of Corneal Endothelial Cell-Like Cells Derived from In-Vitro-Differentiated Human Embryonic Stem Cells. Stem Cells and Development (2014), 23(12), 1340-1354. (Year: 2014).*

(Continued)

*Primary Examiner* — Sean C. Barron
(74) *Attorney, Agent, or Firm* — Cesari & McKenna, LLP (57) ABSTRACT

Provided is a means for identifying cells suitable for transplantation into a cornea, or a means for producing a cell population suitable for transplantation into a cornea using the same. A method for producing a cell population suitable for transplantation into a cornea, the method comprising the steps of (1) preparing a cell population cultured under conditions suitable for inducing differentiation into corneal endothelial cells, and (2) measuring the expression of at least one gene selected from the group consisting of POU6F2, LMX1B, and TFAP2B in the cell population.

18 Claims, 9 Drawing Sheets

(51) Int. Cl.
| | |
|---|---|
| *C12Q 1/6869* | (2018.01) |
| *A61K 35/545* | (2015.01) |
| *C12N 5/079* | (2010.01) |
| *A61K 35/30* | (2015.01) |
| *C12Q 1/6883* | (2018.01) |
| *A61K 35/28* | (2015.01) |

(52) U.S. Cl.
CPC .............. *A61L 27/38* (2013.01); *C12N 5/0621* (2013.01); *C12Q 1/06* (2013.01); *C12Q 1/6869* (2013.01); *A61K 35/28* (2013.01); *C12Q 1/6883* (2013.01); *C12Q 2600/158* (2013.01)

(56) References Cited

U.S. PATENT DOCUMENTS

| | | |
|---|---|---|
| 2016/0266114 A1 | 9/2016 | Koizumi et al. |
| 2017/0253855 A1 | 9/2017 | Nishida et al. |
| 2018/0010093 A1 | 1/2018 | Nishida et al. |

FOREIGN PATENT DOCUMENTS

| | | | | |
|---|---|---|---|---|
| JP | 2006/187281 A | | 7/2006 | |
| JP | 2009/268433 A | | 11/2009 | |
| WO | WO-2011014740 A2 | * | 2/2011 | .............. C12N 15/85 |
| WO | WO-2014/007402 A1 | | 1/2014 | |
| WO | WO-2015/016371 A1 | | 2/2015 | |
| WO | WO-2016/035874 A1 | | 3/2016 | |
| WO | WO-2016/114285 A1 | | 7/2016 | |

OTHER PUBLICATIONS

E. Jensen. Technical Review: In Situ Hybridization. The Anatomical Record (2014), 297, 1349-1353. (Year: 2014).*
Peh et al. Cultivation of Human Corneal Endothelial Cells Isolated from Paired Donor Corneas. PLoS One (2011), 6(12), e28310, 10 pages. (Year: 2011).*
Zhao et al. A Heart-Hand Syndrome Gene: Tfap2b Plays a Critical Role in the Development and Remodeling of Mouse Ductus Arteriosus and Limb Patterning. PLoS One (2011), 6(7): e22908, 8 pages. (Year: 2011).*
Chen et al "Identification of Novel Molecular Markers Through Transcriptomic Analysis in Human Fetal and Adult Corneal Endothelial Cells" Human Molecular Genetics vol. 22, pp. 1271-1279, 2013.
Djebali et al "Landscape of Transcription in Human Cells" Nature vol. 489, pp. 101-108, 2012.
Fiorino et al "Retina-Derived POU Domain Factor 1 Coordinates Expression of Genes Relevant to Renal and Neuronal Development" The International Journal of Biochemistry and Cell Biology vol. 78, pp. 162-172, 2016.
Hara et al "Regulation of Expression of Corneal Endothelial Marker in Transcription Factor AP-2beta" Regenerative Medicine vol. 16, p. 270, O-06-3, 2017.
Kanamori-Katayama et al "Unamplified Cap Analysis of Gene Expression on a Single-Molecule Sequencer" Genome Research vol. 21, pp. 1150-1159, 2011.
Kanatsu-Shinohara et al "Long-Term Proliferation in Culture and Germline Transmission of Mouse Male Germline Stem Cells" Biology of Reproduction vol. 69, pp. 612-616, 2003.

Matsui et al "Derivation of Pluripotential Embryonic Stem Cells from Murine Primordial Germ Cells in Culture" Cell vol. 70, pp. 841-847, 1992.
Perotti et al "Germline Mutations of the POU6F2 Gene in Wilms Tumors with Loss of Heterozygosity on Chromosome 7p14" Human Mutation vol. 24, pp. 400-407, 2004.
Resnick et al "Long-Term Proliferation of Mouse Primordial Germ Cells in Culture" Nature vol. 359, pp. 550-551, 1992.
Robinson et al "EdgeR: A Bioconductor Package for Differential Expression Analysis of Digital Gene Expression Data" Bioinformatics vol. 26, pp. 139-140, 2010.
Satoda et al "Mutations in TFAP2B Cause Char Syndrome, a Familial Form of Patent Ductus Arteriosus" Nature Genetics vol. 25, pp. 42-46, 2000.
Toma et al "Isolation of Multipotent Adult Stem Cells from the Dermis of Mammalian Skin" Nature Cell Biology vol. 3, pp. 778-784, 2001.
Yoshihara et al "Discovery of Molecular Markers to Discriminate Corneal Endothelial Cells in the Human Body" PLoS One vol. 10, pp. 1-14, 2015.
Yoshihara et al "Restricted Presence of POU6F2 in Human Corneal Endothelial Cells Uncovered by Extension of the Promoter-Level Expression Atlas" EBioMedicine vol. 25, pp. 175-186, 2017.
Zhou et al "Retina-Derived POU-Domain Factor-1: A Complex POU-Domain Gene Implicated in the Development of Retinal Ganglion and Amacrine Cells" The Journal of Neuroscience vol. 16, pp. 2261-2274, 1996.
Chen et al "AP-2β is a Downstream Effector of PITX2 Required to Specify Endothelium and Establish Angiogenic Privilege During Corneal Development" Investigative Ophthalmology and Visual Science vol. 57, pp. 1072-1081, 2016.
Chng et al "High Throughput Gene Expression Analysis Identifies Reliable Expression Markers of Human Corneal Endothelial Cells" PLoS ONE vol. 8, e67546, 2013.
Extended Search Report issued in European Application No. 18 821 289.8 dated Mar. 11, 2021.
Frausto et al "Transcriptomic Analysis of Cultured Corneal Endothelial Cells as a Validation for their Use in Cell Replacement Therapy" Cell Transplantation vol. 25, pp. 1159-1176, 2016.
Hara et al "Identification and Potential Application of Human Corneal Endothelial Progenitor Cells" Stem Cells and Development vol. 23, pp. 2190-2201, 2014.
Ju et al "Derivation of Corneal Endothelial Cell-Like Cells from Rat Neural Crest Cells In Vitro" PLoS ONE vol. 7, e42378, 2012.
Liu et al "Lmx1b is Required for Murine Trabecular Meshwork Formation and for Maintenance of Corneal Transparency" Developmental Dynamics vol. 239, pp. 2161-2171, 2010.
Martino et al "Conditional Deletion of AP-2β in Mouse Cranial Neural Crest Results in Anterior Segment Dysgenesis and Early-Onset Glaucoma" Disease Models and Mechanisms vol. 9, pp. 849-861, 2016.
Notification of Reason for Refusal issued in Korean Application No. 10-2019-7038464 dated Feb. 1, 2021.
Pressman et al "Lmx1b, a LIM Homeodomain Class Transcription Factor, is Necessary for Normal Development of Multiple Tissues in the Anterior Segment of the Murine Eye" Genesis vol. 26, pp. 15-25, 2000.
Yu et al "Differentiation of Mouse Induced Pluripotent Stem Cells into Corneal Epithelial-Like Cells" Cell Biology International vol. 37, pp. 87-94, 2013.

\* cited by examiner

CORNEAL ENDOTHELIAL CELL MARKER AND USE THEREOF

CROSS-REFERENCE TO RELATED APPLICATIONS

This application is the National Stage of International Application No. PCT/JP2018/023185, filed Jun. 19, 2018, which claims the benefit of priority of Japanese Patent Application No. 2017-119,518, filed Jun. 19, 2017, the contents of both being incorporated by reference in their entirety for all purposes.

TECHNICAL FIELD

Techniques relating to the identification, evaluation, and production of corneal endothelial cells are disclosed.

BACKGROUND ART

Human corneal endothelial cells basically do not regenerate once injured in vivo, and the number of cells irreversibly decreases. A significantly reduced cell density results in bullous keratopathy, and the transparency of the cornea is lost, thereby leading to visual impairment. Corneal transplantation using donor corneas has been performed so far; however, corneal endothelial damage is the number one adaptation disease of corneal transplantation, and the lack of donor corneas is a serious problem.

Currently, corneal endothelium regeneration therapy using somatic stem cells and pluripotent stem cells has been developed. However, since there is no highly reliable corneal endothelial cell-specific marker, it is not easy to identify corneal endothelial cells, which are the final target products. Until now, some molecules have been reported to be able to serve as markers for corneal endothelial cells (PTL 1). However, no marker for identifying mature corneal endothelial cells has been reported, and molecular mechanisms relating to maturation of corneal endothelial cells have not been clear.

CITATION LIST

Patent Literature

PTL 1: WO2016/035874

SUMMARY OF INVENTION

Technical Problem

An object is to provide a means for identifying cells suitable for corneal transplantation, and a means for producing cells suitable for corneal transplantation using the same.

Solution to Problem

As a result of extensive research, the inventors found that a specific gene can be a specific marker for corneal endothelial cells. After further research and examination based on this finding, the following inventions are provided.

Item A1.
A method for producing a cell population suitable for transplantation into a cornea, the method comprising the steps of:
(1) preparing a cell population cultured under conditions suitable for inducing differentiation into corneal endothelial cells; and
(2) measuring the expression of at least one gene selected from the group consisting of POU6F2, LMX1B, and TFAP2B in the cell population.

Item A2.
The method according to Item A1, wherein the expression level of the gene in the cell population suitable for transplantation into the cornea is equal to or higher than a reference value.

Item A3.
The method according to Item A1 or A2, wherein step (1) is a step of culturing stem cells under conditions suitable for inducing differentiation into corneal endothelial cells.

Item A4.
The method according to any one of Items A1 to A3, wherein step (1) is continued until the expression level of the gene is equal to or higher than a reference value.

Item A5.
The method according to any one of Items A1 to A4, wherein the gene is at least one gene selected from the group consisting of POU6F2 and LMX1B.

Item B1.
A method for determining whether a cell population cultured under conditions suitable for inducing differentiation into corneal endothelial cells is suitable for transplantation into a cornea, the method comprising measuring the expression of at least one gene selected from the group consisting of POU6F2, LMX1B, and TFAP2B in the cell population.

Item B2.
The method according to Item B1, wherein the cell population is a cell population of stem cells cultured under conditions suitable for inducing differentiation into corneal endothelial cells.

Item B3.
The method according to Item B1 or B2, wherein when the expression level of the gene is equal to or higher than a reference value, it is determined that the cell population is suitable for transplantation into the cornea.

Item B4.
The method according to any one of Items B1 to B3, wherein the gene is at least one gene selected from the group consisting of POU6F2 and LMX1B.

Item C1.
A method for producing a cell population suitable for transplantation into a cornea, the method comprising the steps of:
(1) preparing a cell population cultured under conditions suitable for culturing corneal endothelial cells; and
(2) measuring the expression of at least one gene selected from the group consisting of POU6F2, LMX1B, and TFAP2B in the cell population.

Item C2.
The method according to Item C1, wherein the expression level of the gene in the cell population suitable for transplantation into the cornea is equal to or higher than a reference value.

Item C3.
The method according to Item C1 or C2, wherein in step (1), the cell population cultured under conditions suitable for culturing corneal endothelial cells comprises cells obtained from a corneal endothelium.

Item C4.

The method according to any one of Items C1 to C3, wherein the gene is at least one gene selected from the group consisting of POU6F2 and LMX1B.

Item D1.

A method for determining whether a cell population cultured under conditions suitable for culturing corneal endothelial cells is suitable for transplantation into a cornea, the method comprising measuring the expression of at least one gene selected from the group consisting of POU6F2, LMX1B, and TFAP2B in the cell population.

Item D2.

The method according to Item D1, wherein the cell population cultured under conditions suitable for culturing corneal endothelial cells comprises cells obtained from a corneal endothelium.

Item D3.

The method according to Item D1 or D2, wherein when the expression level of the gene is equal to or higher than a reference value, it is determined that the cell population is suitable for transplantation into the cornea.

Item D4.

The method according to any one of Items D1 to D3, wherein the gene is at least one gene selected from the group consisting of POU6F2 and LMX1B.

Item E1.

A method for producing a suspension, sheet, or sphere comprising a cell population, the method comprising the steps of:
(1) preparing a cell population cultured under conditions suitable for inducing differentiation into corneal endothelial cells;
(2) measuring the expression of at least one gene selected from the group consisting of POU6F2, LMX1B, and TFAP2B in the cell population; and
(3) preparing a suspension, sheet, or sphere comprising the cell population that expresses the gene.

Item E2.

The method according to Item E1, wherein step (1) is a step of culturing stem cells under conditions suitable for inducing differentiation into corneal endothelial cells.

Item E3.

The method according to Item E1 or E2, wherein the gene is at least one gene selected from the group consisting of POU6F2 and LMX1B.

Item F1.

A method for treating a patient in need of corneal transplantation, the method comprising the steps of:
(1) preparing a cell population cultured under conditions suitable for inducing differentiation into corneal endothelial cells;
(2) measuring the expression of at least one gene selected from the group consisting of POU6F2, LMX1B, and TFAP2B in the cell population; and
(3) administering the cell population that expresses the gene into the patient.

Item F2.

The method according to Item F1, wherein step (1) is a step of culturing stem cells under conditions suitable for inducing differentiation into corneal endothelial cells.

Item F3.

The method according to Item F1 or F2, wherein the gene is at least one gene selected from the group consisting of POU6F2 and LMX1B.

Item G1.

A method for producing a suspension comprising a cell population, the method comprising the steps of:
(1) preparing a cell population cultured under conditions suitable for culturing corneal endothelial cells;
(2) measuring the expression of at least one gene selected from the group consisting of POU6F2, LMX1B, and TFAP2B in the cell population; and
(3) preparing a suspension, sheet, or sphere comprising the cell population that expresses the gene.

Item G2

The method according to Item G1, wherein the cell population cultured under conditions suitable for culturing corneal endothelial cells comprises cells obtained from a corneal endothelium.

Item G3.

The method according to Item G1 or G2, wherein the gene is at least one gene selected from the group consisting of POU6F2 and LMX1B.

Item H1.

A method for treating a patient in need of corneal transplantation, the method comprising the steps of:
(1) preparing a cell population cultured under conditions suitable for culturing corneal endothelial cells;
(2) measuring the expression of at least one gene selected from the group consisting of POU6F2, LMX1B, and TFAP2B in the cell population; and
(3) administering the cell population that expresses the gene into the patient.

Item H2.

The method according to Item H1, wherein the cell population cultured under conditions suitable for culturing corneal endothelial cells comprises cells obtained from a corneal endothelium.

Item H3.

The method according to Item H1 or H2, wherein the gene is at least one gene selected from the group consisting of POU6F2 and LMX1B.

Item I1.

Use of at least one gene selected from the group consisting of POU6F2, LMX1B, and TFAP2B for determining whether a cell population is suitable for transplantation into a cornea.

Item I2.

The method according to Item I1, wherein the gene is at least one gene selected from the group consisting of POU6F2 and LMX1B.

Advantageous Effects of Invention

In an embodiment, a means for determining whether a cell population is suitable for corneal transplantation is provided. In an embodiment, a means for efficiently producing a cell population suitable for corneal transplantation is provided.

DESCRIPTION OF EMBODIMENTS

The above representative inventions are mainly described below.

The "cell population" means a population comprising a plurality of cells. The individual cells forming the cell population may be the same type of cells or different types of cells.

The "conditions suitable for inducing differentiation into corneal endothelial cells" refer to conditions that are known (or will be developed in the future) as conditions suitable for inducing differentiation of cells into corneal endothelial cells. Examples of the conditions suitable for inducing differentiation into corneal endothelial cells include the conditions disclosed in WO2013/051722, WO2016/114242, WO2016/114285, or WO2016/035874. WO2013/051722, WO2016/114242, WO02016/114285, and WO2016/035874 are incorporated herein by reference. The "cell population cultured under conditions suitable for inducing differentiation into corneal endothelial cells" can be rephrased as "cell population induced to differentiate into corneal endothelial cells." The cell population induced to differentiate into corneal endothelial cells can include corneal endothelial cells and/or corneal endothelial precursor cells.

The medium used for inducing differentiation into corneal endothelial cells is not limited, as long as the object thereof is achieved. In an embodiment, the medium is preferably a serum-free medium. The serum-free medium means a medium that does not contain unconditioned or unpurified serum. A medium containing purified blood-derived components or animal tissue-derived components (e.g., growth factors) corresponds to the serum-free medium.

Examples of usable media include DMEM medium, BME medium, αMEM medium, serum-free DMEM/F12 medium, BGJb medium, CMRL 1066 medium, Glasgow MEM medium, Improved MEM Zinc Option medium, IMDM medium, Medium 199 medium, Eagle MEM medium, Ham medium, RPMI 1640 medium, Fischer's medium, McCoy's medium, Williams E medium, Essential8 Medium, mTeSR1 (Stemcell Technologies), TeSR-E8 medium (Stemcell Technologies), StemSure (Wako Pure Chemical Industries), mESF medium (Wako Pure Chemical Industries), StemFit (Ajinomoto), S-medium (DS Pharma), ReproXF (Reprocell), PSGro-free Human iPSC/ESC Growth Medium (StemRD), hPSC Growth Medium (Takara Bio), ReproFF2 (Reprocell), EX-CELL 302 medium (SAFC), KnockOutTMDMEM, Medium 154, StemPro (registered trademark) hESC SFM, EX-CELL-CD-CHO (SAFC), STEMdif-fAPEL Medium (Stemcell Technologies), mixtures thereof, and like media that can be used for culturing animal cells. In an embodiment, the medium is preferably a medium for stem cells.

The medium may contain a serum replacement. Examples of serum replacements include albumin (e.g., lipid-rich albumin), transferrin, fatty acid, collagen precursor, trace elements (e.g., zinc and selenium), B-27 (registered trademark) supplement, N2 supplement, knockout serum replacement (KSR: produced by Invitrogen), 2-mercaptoethanol, 3'-thiolglycerol, and the like. For example, in the case of B-27 supplement, the concentration of the serum replacement in the medium is 0.01 to 10 wt % or 0.5 to 4 wt %.

Various substances can be added to the medium for the purpose of cell maintenance and growth and/or differentiation induction. Examples of such substances include carbon sources, such as glycerol, glucose, fructose, sucrose, lactose, honey, starch, and dextrin; hydrocarbons, such as fatty acids, fats and oils, lecithin, and alcohols; nitrogen sources, such as ammonium sulfate, ammonium nitrate, ammonium chloride, urea, and sodium nitrate; inorganic salts, such as common salt, potassium salt, phosphate salt, magnesium salt, calcium salt, iron salt, and manganese salt; monopotassium phosphate, dipotassium phosphate, magnesium sulfate, sodium chloride, ferrous sulfate, sodium molybdate, sodium tungstate, manganese sulfate, various vitamins, amino acids, and the like.

The medium may or may not contain a differentiation inducer, such as BMP4 (bone morphogenetic protein 4), a transforming growth factor, and activin. In an embodiment, it is preferable that the medium is substantially free of one or more, two or more, or all of the above differentiation inducers. Here, the phrase "substantially free" means, for example, that the concentration is less than 0.5 nM or an undetectable level.

The medium may contain or may not contain differentiation induction promoters, such as high-concentration retinoic acid, BMP inhibitors, TGFβ inhibitors, and Noggin. The "high-concentration retinoic acid" refers to 1 μM retinoic acid, and particularly about 10 μM retinoic acid.

In an embodiment, it is preferable that the medium is substantially free of one or more, two or more, or all of the above differentiation induction promoters. The medium may contain or may not contain Wnt, Wnt signal activators, Chordin, etc. In an embodiment, the medium is preferably substantially free of these components.

In an embodiment, the medium preferably contains one or more, two or more, three or more, four or more, or all differentiation-inducing factors selected from the group consisting of GSK3 inhibitors, retinoic acid, TGFb2, insulin, and ROCK inhibitors.

The pH of the medium can be adjusted within a range of 5.5 to 9.0, 6.0 to 8.0, or 6.5 to 7.5. The culture temperature can be set to 36° C. to 38° C. or 36.5° C. to 37.5° C. Culture can be performed in an atmosphere of 1% to 25% $O_2$ and 1% to 15% $CO_2$.

The time period for culture is not particularly limited, and can be set, for example, in the range of 1 week to 8 weeks, 2 weeks to 6 weeks, or 3 weeks to 5 weeks.

For culture, any container used for cell culture can be used. Examples of such containers include microplates, microwell plates, multiplates, multiwell plates, micro slides, chamber slides, schales, flasks, tissue culture flasks, dishes, Petri dishes, tissue culture dishes, multidishes, tubes, trays, cell culture bags, and roller bottles.

The inner surface of the culture container may be coated with one or more members selected from collagen, fibronectin, laminin, laminin fragments (e.g., laminin E8 fragment and laminin 511E8 fragment), vitronectin, basement membrane matrix, gelatin, hyaluronic acid, polylysine, vitronectin, and hyaluronic acid.

There is no particular limitation on the type of cells to be cultured under conditions suitable for inducing differentiation into corneal endothelial cells. In an embodiment, the cells are preferably stem cells. Examples of stem cells include artificial pluripotent stem cells (induced pluripotent stem cells: iPS cells), embryonic stem cells (ES cells), fetal primordial germ cell-derived pluripotent stem cells (EG cells), testis-derived pluripotent stem cells (GS cells), and human somatic stem cells capable of differentiating into corneal endothelial cells (tissue stem cells). In an embodiment, the stem cells are preferably iPS cells.

iPS cells can be obtained by any methods, including known methods and methods that will be developed in the future. For example, iPS cells can be obtained by introducing DNA- or protein-form specific reprogramming factors into somatic cells. Examples of reprogramming factors include Oct3/4, Sox2, Sox1, Sox3, Sox15, Sox17, Klf4, Klf2, c-Myc, N-Myc, L-Myc, Nanog, Lin28, Fbx15, ERas, ECAT15-2, Tcl1, beta-catenin, Lin28b, Sall1, Sall4, Esrrb, Nr5a2, Tbx3, and Glis1. These reprogramming factors may be used singly or in any combination. Examples of combinations of reprogramming factors are disclosed in, for example, WO2007/069666, WO2008/118820, WO2009/007852, WO2009/032194, WO2009/058413, and WO2009/057831. The type of somatic cells is not particularly limited, and somatic cells for use include any cells that have been confirmed to produce iPS cells and any cells hereafter reported to produce iPS cells. In an embodiment, examples of preferable somatic cells include fibroblasts and white blood cells. The somatic cells are preferably derived from humans.

ES cells are obtained by any available technique. For example, ES cells can be established by removing the inner cell mass from the blastocyst of a fertilized egg from a mammal (preferably, a human), and culturing the inner cell mass on a feeder of fibroblasts. The mammal is not particularly limited, but is preferably a human. ES cells in passage culture can be maintained using a culture solution containing substances, such as a leukemia inhibitory factor (LIF) and/or a basic fibroblast growth factor (bFGF). ES cells can be selected, for example, using expression of gene markers, such as OCT-3/4, NANOG, and ECAD, as an indication.

EG cells are pluripotent cells as with ES cells, and are established from primordial germ cells in the fetal stage. EG cells are established by culturing primordial germ cells in the presence of substances, such as LIE, bFGF, and stem cell factors (Y. Matsui et al. (1992), Cell, 70: 841-847; J. L. Resnick et al. (1992), Nature, 359: 550-551).

GS cells are testis-derived pluripotent stem cells, and are the origin of sperm formation. These cells can be induced to differentiate into a variety of cell lineages like ES cells. GS cells can be self-renewed in a culture solution containing a glial cell line-derived neurotrophic factor (GDNF). Repeated passage under the same conditions as those for ES cells produces sperm stem cells (M. Kanatsu-Shinohara et al. (2003) Biol. Reprod., 69: 612-616).

Examples of somatic stem cells that can be differentiated into corneal endothelial cells include neural crest stem cells derived from the corneal stroma (COPs), mesenchymal stem cells, and skin-derived pluripotent precursor cells (skin-derived precursors: SKPs), with COPs and SKPs being preferable. COPs can be prepared, for example, by removing the epithelium and endothelium from a cornea, treating the corneal stroma with a collagenase, and culturing the separated cells in a DMEM/F12 medium containing EGF, FGF2, B27 supplements and LIE SKPs can be prepared, for example, in accordance with the procedure described in Nat Cell Biol., 2001, vol. 3, 778-784.

The "conditions suitable for culturing corneal endothelial cells" refer to conditions suitable for growing corneal endothelial cells while maintaining their characteristics. The "conditions suitable for culturing corneal endothelial cells" may or may not be conditions under which corneal endothelial cells can be grown. The "conditions suitable for culturing corneal endothelial cells" include conditions known to be suitable for growing corneal endothelial cells while maintaining their characteristics (e.g., the conditions disclosed in WO2014/104366), and conditions that will be developed in the future as such conditions. The cell population cultured under conditions suitable for culturing corneal endothelial cells can include corneal endothelial cells and/or corneal endothelial precursor cells.

Specific examples of the conditions suitable for culturing corneal endothelial cells include culture conditions in a medium generally used for culturing the animal cells described above. In an embodiment, glucose can be added to the medium. The glucose concentration of the medium can be adjusted to 2.0 g/L or less, or 0.1 to 1.0 g/L. In an embodiment, it is preferable to add to the medium a growth factor such as a hepatocyte growth factor (HGF), an epidermal growth factor (EGF), recombinant EGF (rEGF), insulin and/or fibroblast growth factor (FGF). Of these factors, a single factor or a combination of two or more factors may be added to the medium. The concentration of the growth factor(s) in the medium is typically 1 to 100 ng/mL, and preferably 2 to 5 ng/mL. From the standpoint of efficient culture of corneal endothelial cells, it is preferable to add a 5 to 1,000 µg/mL ascorbic acid derivative, such as ascorbic acid 2-phosphate, to the medium. In addition, the pH and temperature of the medium, the culture container, etc., may be as described above. The time period for culture is not particularly limited, and, for example, cells can be cultured until the stage at which the cells become confluent (steady state) (e.g., 1 to 5 days). In an embodiment, a conditioned medium of mesenchymal stem cells (MSC) is preferably used for culturing corneal endothelial cells.

There is no particular limitation on the type of cells cultured under conditions suitable for culturing corneal endothelial cells. Usable examples include corneal endothelial cells isolated from a cornea, or cells, other than corneal endothelial cells, obtained by inducing differentiation into corneal endothelial cells (e.g., cells obtained by inducing differentiation under the above-described "conditions suitable for inducing differentiation into corneal endothelial cells").

There is no particular limitation on the means for isolating corneal endothelial cells from a cornea, and any method known or hereafter developed in the art can be suitably selected for use. For example, a Descemet's membrane is removed from human corneoscleral rim with corneal endothelial cells attached to the Descemet's membrane, and shredded, followed by culture in a medium containing about 0.2% of collagenase in 5% $CO_2$ at 37° C. for 1 to 3 hours. A usable medium is a DME medium containing 15% fetal calf serum (FCS) and a 2 ng/mL basic fibroblast growth factor (bFGF). The fibroblasts are then removed by centrifugation wash, followed by tryptic digestion, thereby obtaining a cell population containing pellet-like corneal endothelial cells (primary culture cells).

"POU6F2" is a gene encoding a transcription factor belonging to the POU family having a POU homeodomain. Expression thereof in the central nervous system, retina ganglion cells, and amacrine cells has been reported, and POU6F2 is also referred to as "retina-derived POU-domain factor-1" (RPF-1) (Zhou H et al. J Neurosci. 1996. PMID: 8601806). Further, germline mutations have been reported in patients with Wilms' tumors, and it is suggested that POU6F2 is responsible for gene expression control in the stage of kidney development (Perotti D et al. Hum Mutat. 2004. PMID: 15459955, Fiorino A et al. Int J Biochem Cell Biol. 2016. PMID: 27425396).

"LMX1B" is a gene encoding a transcription factor belonging to the LIM homeodomain family. LMX1B is known as a causative gene for nail-patella syndrome, and has been reported to be involved not only in the development of limbs, but also in the development of the glomerular basement membrane of the kidney.

"TFAP2B" is a gene encoding a transcription factor belonging to the AP-2 family. TFAP2B has been reported as a causative gene for Char syndrome mainly with facial dysmorphism, patent ductus arteriosus, and aplasia or hypoplasia of the middle phalanges of the fifth fingers (Satoda M et al. Nat Genet. 2000. PMID: 10802654).

The step of preparing a cell population cultured under conditions suitable for inducing differentiation into corneal endothelial cells can be performed by culturing the above-described cells under the conditions suitable for inducing differentiation into corneal endothelial cells described above. In an embodiment, the cell population cultured under conditions suitable for inducing differentiation into corneal endothelial cells may be a cell population sorted using the presence of a molecule known as a corneal endothelial cell marker as an indication. Examples of corneal endothelial cell markers include the molecules disclosed in WO2009/057831 (e.g., ZP4, MRGPRX3, GRIP1, GLP1R, HTR1D, CLRN1, SCNN1D, PKD1, CNTN6, NSF, CNTN3, PPIP5K1, and PCDHB7). Sorting of a cell population using a corneal endothelial cell marker as an indication can be performed using any method, such as using FACS. In an embodiment, it is preferable to further culture the cell population collected using a corneal endothelial marker as an indication under conditions suitable for inducing differentiation into corneal endothelial cells.

The form of the cell population cultured under conditions suitable for inducing differentiation into corneal endothelial cells is not particularly limited. For example, the cell population can be in the form of a monolayer, a multilayer, a sheet, a sphere, or a suspension, according to a conventional method. In an embodiment, the cell population is preferably in a suspended state. When the cell population cultured under conditions suitable for inducing differentiation into corneal endothelial cells is in a monolayer state, the cell population can be brought into a suspended state according to a conventional method. A suspended cell population can be obtained, for example, by suspending a cell population using a proteolytic enzyme (e.g., trypsin) and/or a chelating agent for destroying cell-cell adhesion molecules. The cell population can be prepared in any form, such as a monolayer, a multilayer, a sheet, a sphere, or a suspension, before or after measuring the expression of at least one gene selected from the group consisting of POU6F2, LMX1B, and TFAP2B.

Measuring the expression of at least one gene selected from the group consisting of POU6F2, LMX1B, and TFAP2B in a cell population cultured under conditions suitable for inducing differentiation into corneal endothelial cells, or a cell population cultured under conditions suitable for culturing corneal endothelial cells, can be performed using any method that is known or will be developed in the future as a method for measuring intracellular gene expression. The measurement is sufficient if the presence or absence of gene expression can be determined; however, in an embodiment, quantitative measurement is preferable. For example, it is preferable to measure (preferably quantitatively measure) the intracellular mRNA of each gene by PCR or the like.

In an embodiment, at least one gene selected from the group consisting of POU6F2, LMX1B, and TFAP2B preferably contains POU6F2 or LMX1B, and preferably POU6F2. In an embodiment, it is preferable to measure only the expression of POU6F2. In another embodiment, it is preferable to measure the expression of a combination of POU6F2 and LMX1B, or a combination of POU6F2, LMX1B, and TFAP2B.

The genes POU6F2, LMX1B, and TFAP2B are specifically expressed in corneal endothelial cells and corneal endothelial precursor cells, as shown in the Examples, described later. Therefore, corneal endothelial cells, or a cell population suitable for transplantation into the cornea, can be obtained using the expression of these genes as an indication. Further, the expression of these genes can be used as an indication to determine whether the cell population is suitable for transplantation into the cornea. That is, if these genes are expressed in the cell population, it can be determined that the cell population is suitable for transplantation into the cornea; and if these genes are not expressed, it can be determined that the cell population is not suitable for transplantation into the cornea. Moreover, POU6F2 is expressed at high levels in relatively mature corneal endothelial cells. Therefore, relatively mature corneal endothelial cells, or a cell population suitable for transplantation into the cornea, can be obtained using the expression or expression levels of POU6F2 as an indication.

The expression of at least one gene selected from the group consisting of POU6F2, LMX1B, and TFAP2B may be or may not be directly measured for all the cells constituting the cell population cultured under conditions suitable for inducing differentiation into corneal endothelial cells. By measuring the gene expression level in some of the cells constituting the cell population, the gene expression level in the remaining cells constituting the cell population can be indirectly measured. In an embodiment, it is preferable that the gene expression is measured in some of the cells constituting the cell population, and that the gene expression in the remaining cells is indirectly measured. This is particularly true when a method involving cell death is employed as a method for measuring gene expression.

A high expression level of at least one gene selected from the group consisting of POU6F2, LMX1B, and TFAP2B in the cell population is an indication that the cell population is suitable for transplantation into the cornea. In an embodiment, the expression level of the gene in the cell population is preferably equal to or higher than a predetermined reference value. The reference value can be determined in any manner from the viewpoint of being suitable for transplantation into the cornea. For example, the reference value can be set equal to or higher than the expression level of the gene in in vivo corneal endothelial cells and/or cultured corneal endothelium.

When the cell population cultured under conditions suitable for inducing differentiation into corneal endothelial cells does not express at least one gene selected from the group consisting of POU6F2, LMX1B, and TFAP2B, or when it is determined that the expression level of at least one gene selected from the group consisting of POU6F2, LMX1B, and TFAP2B in the cells is not sufficient, the cell population can be further cultured under conditions suitable for inducing differentiation into corneal endothelial cells. Such further culture can be continued until the cell population expresses the gene, or until it is determined that the expression level of the gene is sufficient (e.g., until it becomes equal to or higher than the reference value).

Thus, the cell population in which the expression of at least one gene selected from the group consisting of POU6F2, LMX1B, and TFAP2B has been confirmed can be used as a cell population suitable for transplantation into the cornea. The cell population can be used as a cell preparation for regenerating the corneal endothelium. The cell preparation comprising the cell population may contain scaffold materials, components, and other pharmaceutically acceptable carriers for assisting the maintenance or growth of the cell population, or the administration thereof to the affected area. Examples of components for maintaining or growing cells include medium components, such as carbon sources, nitrogen sources, vitamins, minerals, salts, and various cytokines; and extracellular matrix preparations, such as Matrigel™ Examples of the scaffold material or component include biodegradable polymers, such as collagen, polylactic acid, hyaluronic acid, cellulose, and derivatives thereof, and complexes composed of two or more thereof; for example, aqueous solutions for injection, such as physiological saline, media, physiological buffers such as PBS, and isotonic solutions (e.g., D-sorbitol, D-mannose, D-mannitol, and sodium chloride) containing glucose and/or other adjuvants.

The cell preparation may contain a solubilizing agent, such as an alcohol (specifically ethanol), a polyalcohol such as propylene glycol or polyethylene glycol, or a nonionic surfactant such as polysorbate 80 or HCO-50.

Other pharmaceutically acceptable carriers include pharmaceutically acceptable organic solvents, polyvinyl alcohol, polyvinyl pyrrolidone, carboxyvinyl polymer, sodium carboxymethylcellulose, sodium polyacrylate, sodium alginate, water-soluble dextran, sodium carboxymethyl starch, pectin, methylcellulose, ethylcellulose, xanthan gum, gum arabic, casein, agar, polyethylene glycol, diglycerin, glycerin, propylene glycol, petrolatum, paraffin, stearyl alcohol, stearic acid, mannitol, sorbitol, and lactose; as well as surfactants, buffers, emulsifiers, suspending agents, soothing agents, stabilizers, and the like that are acceptable as pharmaceutical additives.

The subjects (patients) to whom the cell preparation is administered are not particularly limited, as long as they are considered to be in need of the cell preparation. Examples of subjects include subjects with hereditary endothelial damage, such as Fuchs corneal endothelial dystrophy, corneal endothelial abnormalities associated with glaucoma, corneal endothelial damage after intraocular surgery, corneal endothelial damage after viral infection such as herpes, and symptoms associated with corneal endothelium reduction after corneal transplantation. In an embodiment, the subjects to whom the cell preparation is administered are patients with corneal endothelial dysfunction (e.g., patients with reduced corneal endothelial cell pump and barrier function), and are patients with bullous keratopathy, corneal edema, corneal vitiligo, and/or keratoconus. The administration form of the cell preparation is not particularly limited. For example, the cell preparation can be injected into the eyeball through an injection needle.

3. Method B for Determining Whether a Cell Population is Suitable for Transplantation into the Cornea In an embodiment, the method for determining whether a cell population is suitable for transplantation into the cornea preferably comprises the step of measuring the expression of at least one gene selected from the group consisting of POU6F2, LMX1B, and TFAP2B in a cell population cultured under conditions suitable for inducing differentiation into corneal endothelial cells.

EXAMPLES

The following Examples describe the present invention in more detail. However, the invention is not limited to the Examples.

Human corneoscleral rim was obtained, a Descemet's membrane was removed under a microscope, and the in vivo corneal endothelium was collected. The collected corneal endothelium was immediately put into RNAlater RNA Stabilization Reagent (QIAGEN Inc., Valencia, Calif.) and stored at −70° C. Then, using the Qiagen miRNeasy Mini Kit (QIAGEN Inc.), total RNA was extracted according to the manufacturer's protocol, and Heliscope CAGE libraries were prepared for three samples (Kanamori-Katayama M, et al. (2011), Genome Res. 21: 1150-1159). Then, sequencing was performed by SeqLL (Boston, Mass.) using the HeliScope™ Single Molecule Sequencer (Helicos BioSciences Corp., Cambridge, Mass.).

The Descemet's membrane isolated as described above was incubated in StemPro Accutase (Thermo Fisher) at 37° C. for 30 minutes, and corneal endothelial cells were isolated from the Descemet's membrane. The isolated corneal endothelial cells were gently centrifuged and collected, and then suspended in a Dulbecco's modified Eagle medium (DMEM) containing 50 U/mL penicillin, 50 µg/mL streptomycin, 10% fetal bovine serum (ICN Biomedicals, Inc., Aurora, Ohio), and 2 ng/mL basic fibroblast growth factor (bFGF; Invitrogen). The cells were seeded on dishes coated with a cell attachment reagent (FNC coating mix; Athena E S, Baltimore, Md.), and incubated at 37° C. in a humidified atmosphere of 5% $CO_2$. Total RNA was then extracted using the Qiagen miRNeasy Mini Kit (QIAGEN Inc.) according to the manufacturer's protocol. All the cells used for RNA extraction were those harvested during the first passage. For this as well, Heliscope CAGE libraries were prepared for two samples. Then, sequencing was performed by SeqLL (Boston, Mass.) using HeliScopeT Single Molecule Sequencer (Helicos BioSciences Corp., Cambridge, Mass.).

The obtained sequence data was mapped using hg19 as a reference genome using Delve (Djebali S, et al. (2012), Nature 489, 101-108). Further, the number of tags mapped to 184,827 promoter regions identified in the FANTOM5 project was counted. For the in vivo corneal endothelium, the expression level was compared with the data of 182 human tissue samples analyzed in FANTOM5, and for the cultured corneal endothelial cells, the expression level was compared with the data of 536 human cultured cell samples analyzed in FANTOM5. Each was corrected by the total number of mapped tags, and the expression level was calculated with tpm (tags per million) as the unit. Differential expression analysis was performed using edgeR (Robinson, M. D. et al., (2010), Bioinformatics 26, 139-140.), and those that satisfied the following conditions were identified as markers for genes specifically expressed on corneal endothelial cells:

1) a false discovery rate (FDR) of less than 0.01 in the corneal endothelium samples and other samples;

2) expression at 10 tpm or more in the corneal endothelium samples;
3) the average expression level in all the samples other than the corneal endothelium was less than 3 tpm;
4) despite the highest expression in all the samples other than the corneal endothelium, the expression level was smaller than the average expression level in the corneal endothelium samples; and
5) the average expression level in corneal endothelium samples was 32 times or more higher than the average expression level in all of the other samples.

From the obtained corneal endothelium-specific gene candidates, TFAP2B, LMX1B, and POU6F2 were identified as transcription factors specifically expressed, in common, on the in vivo corneal endothelium and cultured corneal endothelial cells. As a reference for human transcription factors, a reference was made to http://fantomgsc.riken.jp/5/sstar/Browse_Transcription_Factors_hg19.

Figure 1:
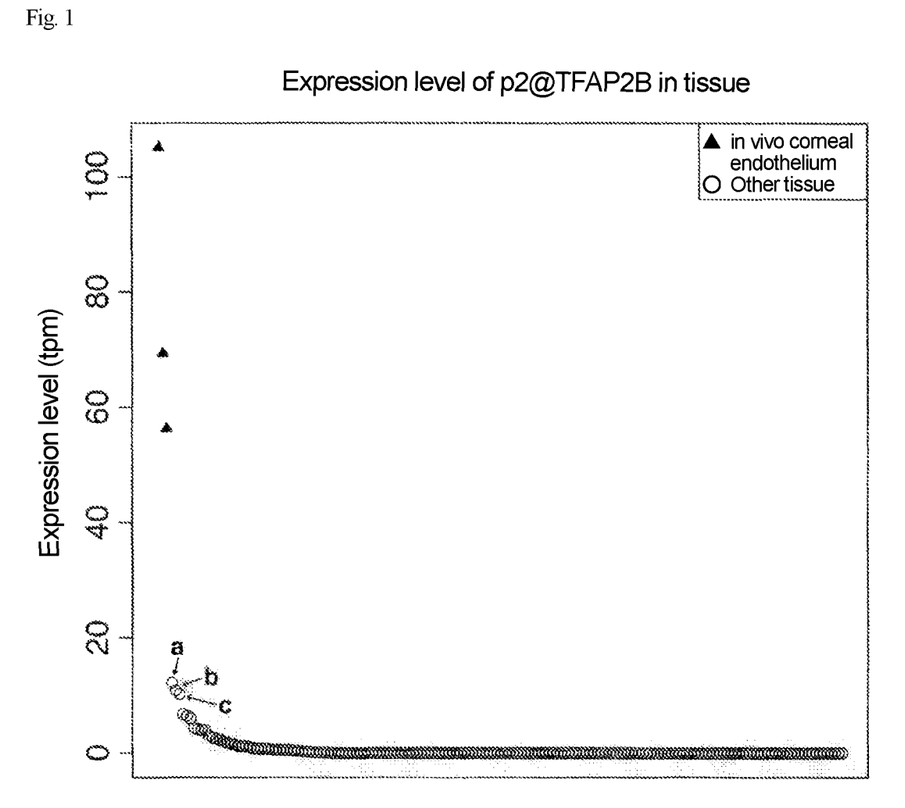
FIG. 1 shows the expression levels of TFAP2B in human tissue samples.

FIG. 1 shows the expression levels of TFAP2B in human tissue samples. a, b, and c show the expression levels of TFAP2B in the midbrain substantia nigra, brainstem locus coeruleus, and epididymis, respectively. It was confirmed that TFAP2B was most highly expressed in the in vivo corneal endothelium.

Figure 2:
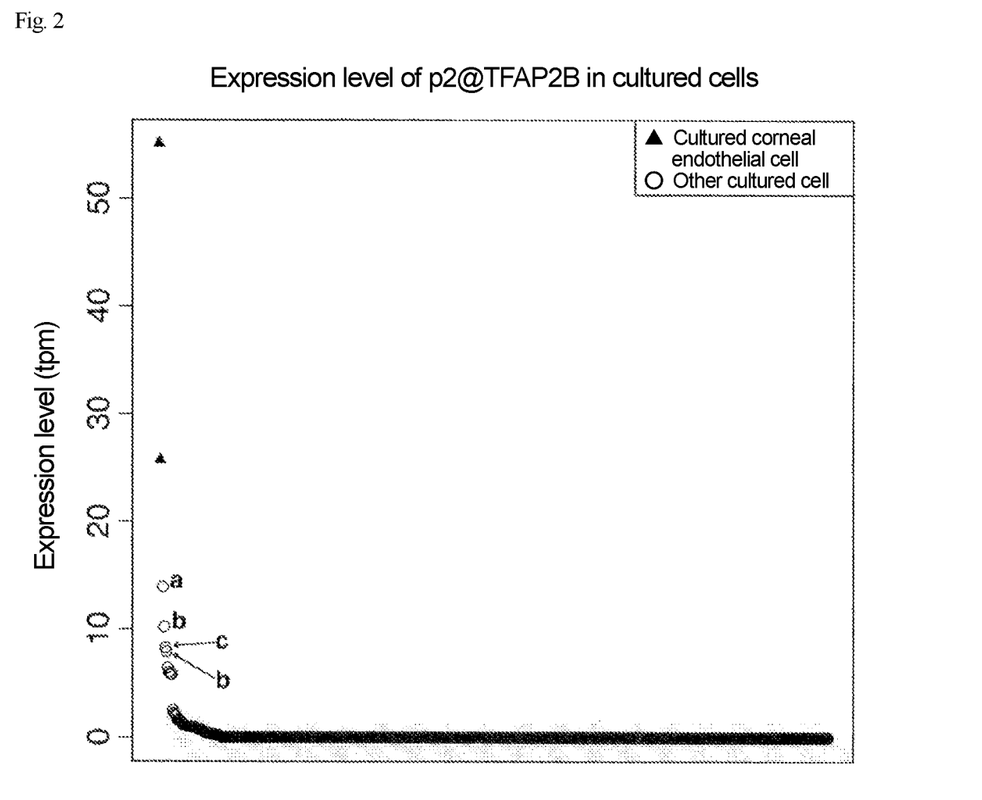
FIG. 2 shows the expression levels of TFAP2B in human cultured cell samples.

FIG. 2 shows the expression levels of TFAP2B in human cultured cell samples. a, b, and c show the expression levels of TFAP2B in olfactory epithelial cells, trabecular meshwork cells, and conjunctival fibroblasts, respectively. It was confirmed that TFAP2B was most highly expressed in the cultured corneal endothelial cells.

Figure 3:
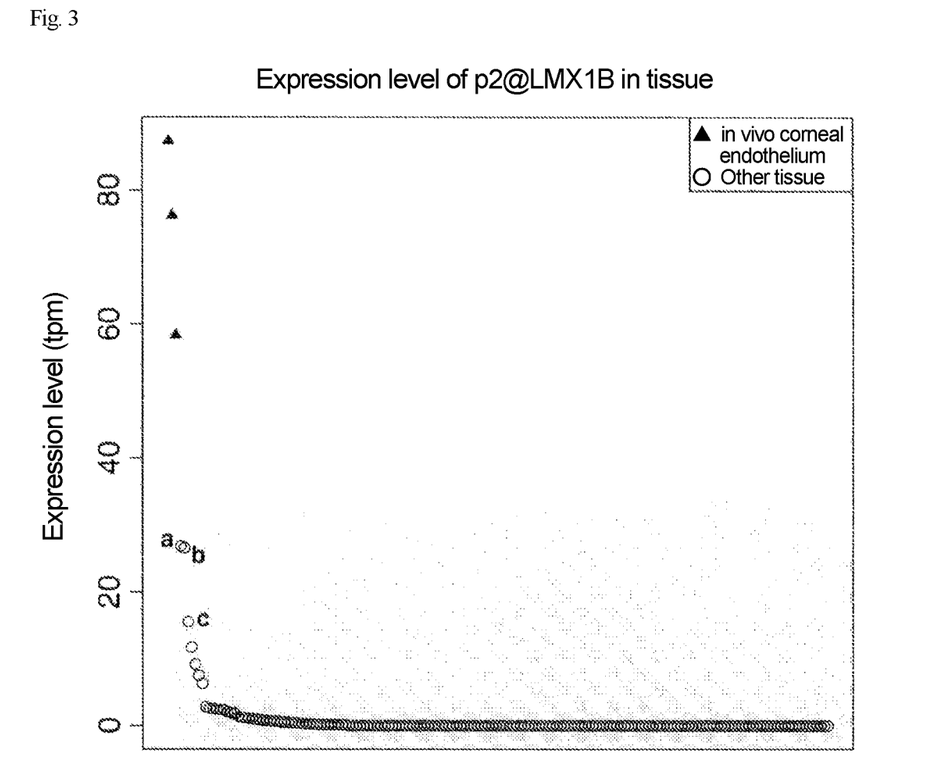
FIG. 3 shows the expression levels of LMX1B in human tissue samples.

FIG. 3 shows the expression levels of LMX1B in human tissue samples. a, b, and c show the expression levels of LMX1B in the parotid gland, salivary gland, and submandibular gland, respectively. It was confirmed that LMX1B was most highly expressed in the in vivo corneal endothelium.

Figure 4:
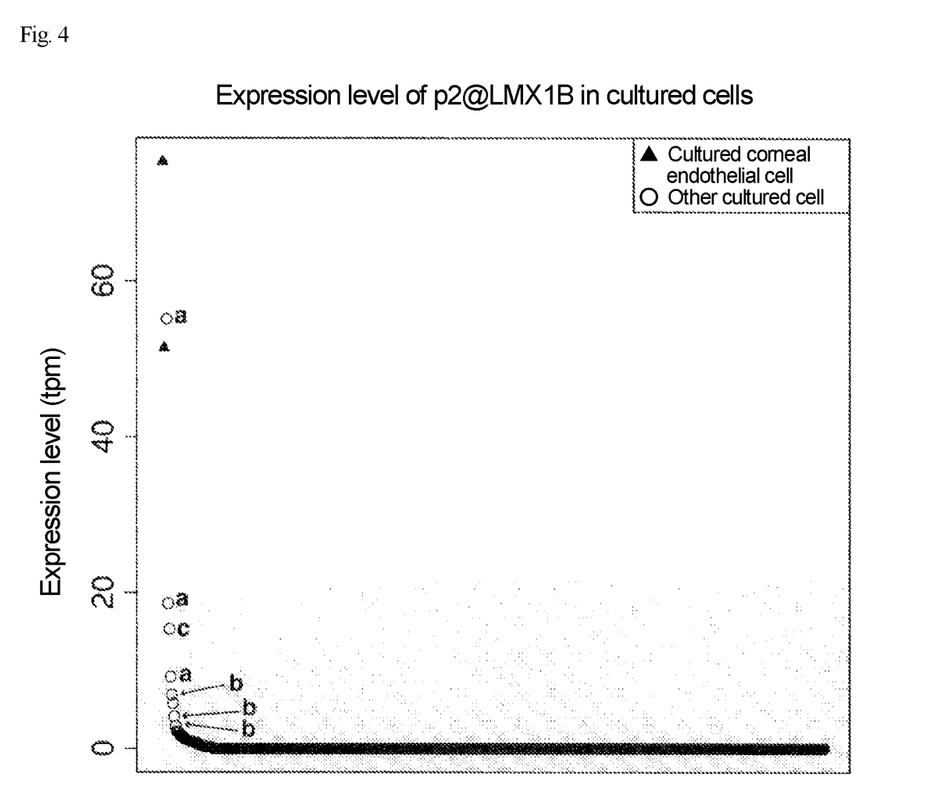
FIG. 4 shows the expression levels of LMX1B in human cultured cell samples.

FIG. 4 shows the expression levels of LMX1B in human cultured cell samples. a, b, and c show the expression levels of LMX1B in trabecular meshwork cells, corneal parenchymal cells, and fibroblasts, respectively. The same level of expression as in the corneal endothelial cells was also observed in the trabecular meshwork cells. Further, expression in the corneal parenchymal cells was also confirmed. Since the corneal endothelium, corneal parenchyma, and trabecular meshwork are all periocular neural crest-derived tissues, these results suggest that LMX1B is expected to be applied not only as a corneal endothelial marker, but also as a marker for periocular neural crest-derived tissues.

Figure 5:
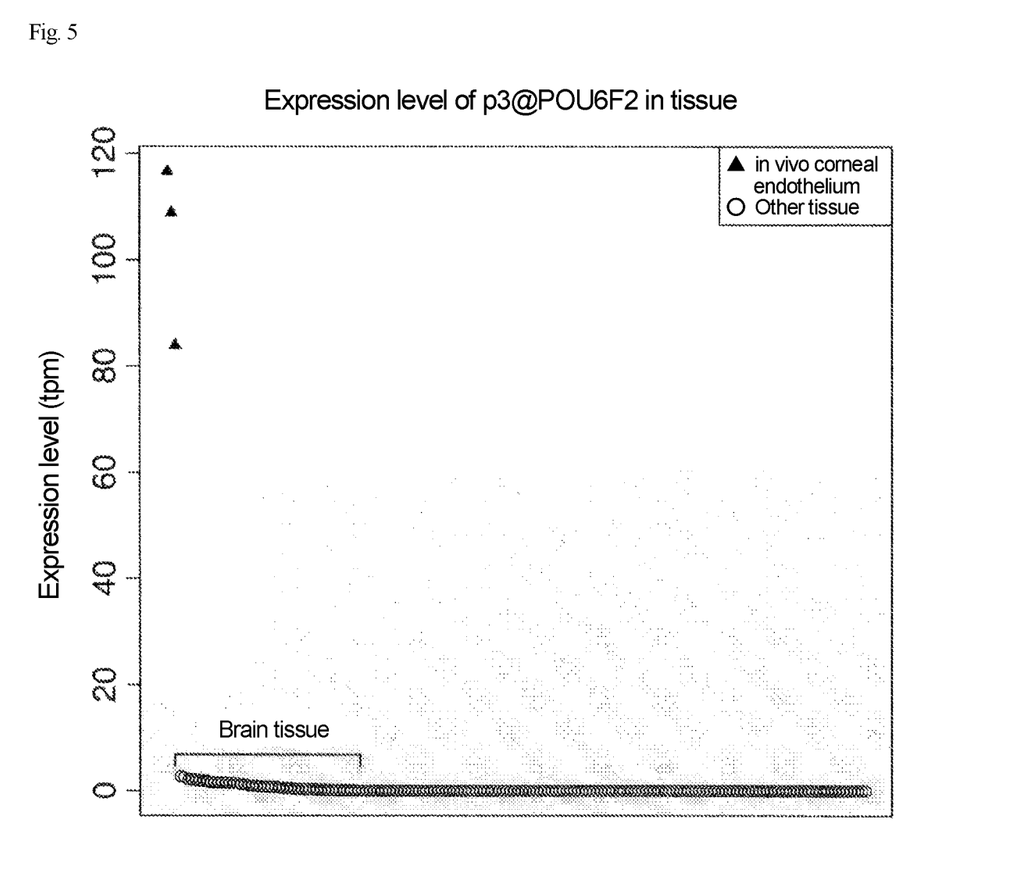
FIG. 5 shows the expression levels of POU6F2 in human tissue samples.

FIG. 5 shows the expression levels of POU6F2 in human tissue samples. Although the expression level in the in vivo corneal endothelium is around 100 tpm, the expression level in brain tissue where expression is observed is less than 10 tpm and is very highly specific.

Figure 6:
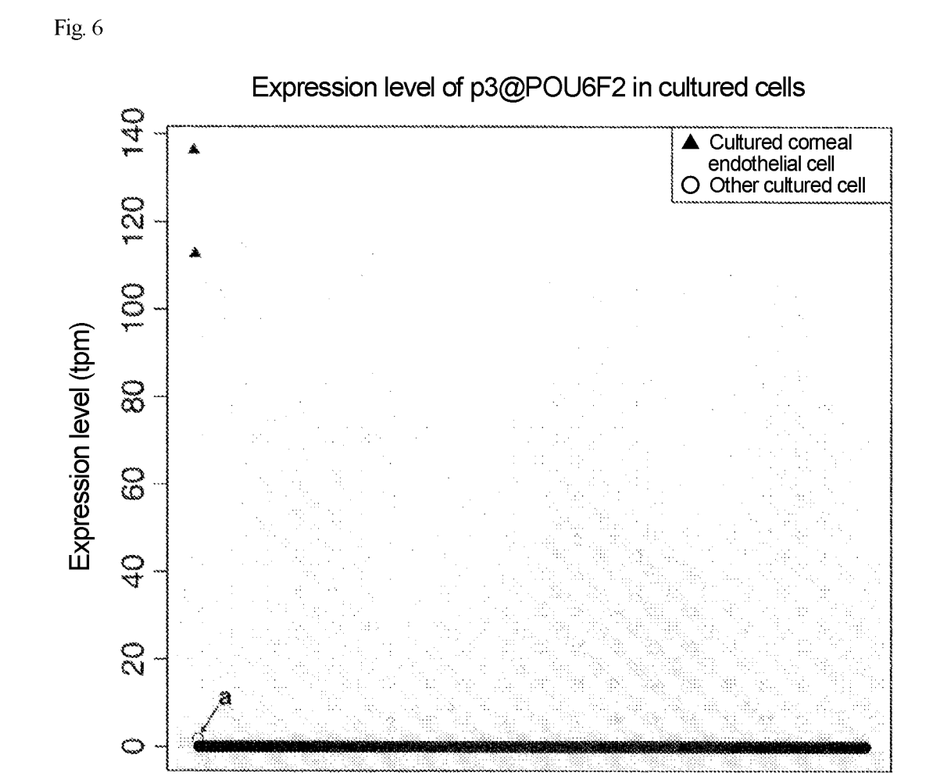
FIG. 6 shows the expression levels of POU6F2 in human cultured cell samples.

FIG. 6 shows the expression levels of POU6F2 in human cultured cell samples. a shows the expression level of POU6F2 in hepatocytes. The expression level in the cultured corneal endothelial cells was 100 tpm or more, whereas no expression was observed in 535 out of the 536 human cultured cell samples analyzed in FANTOM5. The expression level only observed in hepatocytes was as very low as less than 2 tpm.

From the results of FIGS. 1 to 6, POU6F2, LMX1B, and TFAP2B were all significantly highly expressed in corneal endothelial cells; thus, it is considered that they are useful as corneal endothelial cell markers, and can be used for induction of corneal endothelial cells.

Figure 7:
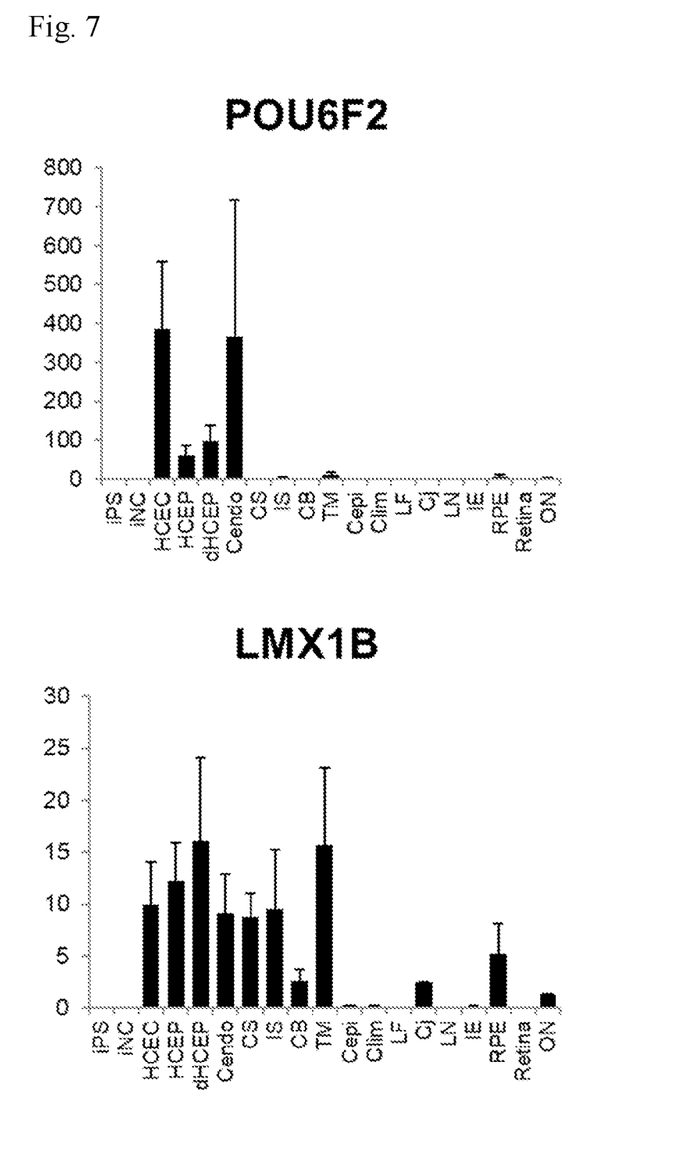
FIG. 7 shows cells induced from iPS cells (iPS) (e.g., neural crest cells (iNC)), and the results of measuring expression in intraocular tissues by quantitative PCR. Abbreviations are used as follows: iPS: iPS cells, iNC: neural crest cells derived from iPS cells, HCEC: cultured corneal endothelial cells, HCEP: corneal endothelial precursor cells, dHCEP: differentiation-induced corneal endothelial precursor cells, Cendo: in vivo corneal endothelium, CS: corneal stroma, IS: iris stroma, CB: ciliary body, TM: trabecular meshwork, Clim: corneal limbal epithelium, Cepi: central corneal epithelium, LF: corneal limbal fibroblasts, Cj: conjunctival epithelium, LN: lens, IE: iris epithelium, RPE: retinal pigment epithelium, Retina: retina, and ON: optic nerve.

The expression of the above three genes was quantitatively analyzed in the corneal endothelium and other tissues. FIG. 7 shows the results of measuring expression in cells induced from iPS cells (iPS) (e.g., neural crest cells (iNC)) and intraocular tissues by quantitative PCR. As shown in FIG. 7, it was confirmed that POU6F2, LMX1B, and TFAP2B were highly expressed in the cultured corneal endothelial cells (HCEC), corneal endothelial precursor cells (HCEP), differentiation-induced corneal endothelial precursor cells (dHCEP), and in vivo corneal endothelium (Cendo). In contrast, POU6F2 was hardly expressed in the corneal stroma (CS), iris stroma (IS), ciliary body (CB), trabecular meshwork (TM), corneal limbal epithelium (Clim), central corneal epithelium (Cepi), corneal limbal fibroblasts (LF), conjunctival epithelium (Cj), lens (LN), iris epithelium (IE), retinal pigment epithelium (RPE), retina (Retina), and optic nerve (ON). LMX1B was also expressed in the trabecular meshwork, corneal parenchyma, and iris stroma, which were neural crest-derived tissues. TFAP2B was highly expressed in the iPS-derived neural crest cells. These results suggest that POU6F2, LMX1B, and TFAP2B are useful as markers for corneal endothelial cells.

Figure 8:
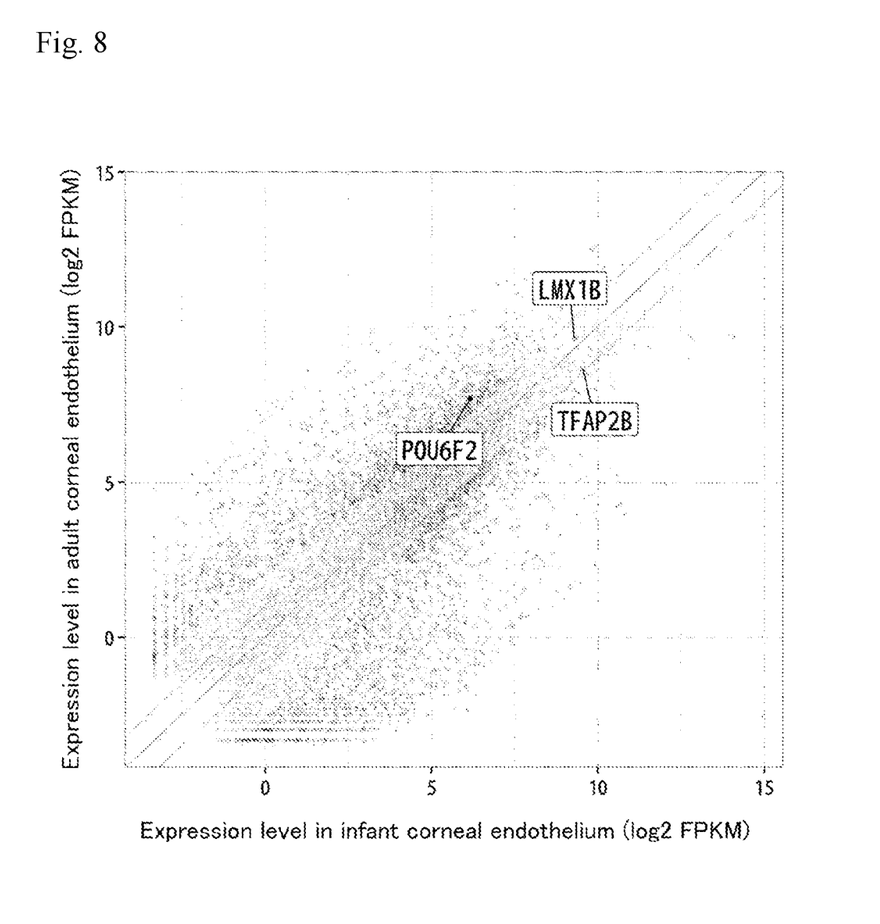
FIG. 8 shows the results of analyzing RNA-seq data in a human adult-derived corneal endothelium and a human fetal-derived corneal endothelium for POU6F2, LMX1B, and TFAP2B.

Analysis of RNA-seq data (Chen Y, et al. (2013), Hum Mol Genet 22: 1271-1279) in the human adult/fetal-derived corneal endothelium revealed no significant changes in the expression of TFAP2B and LMX1B; in contrast, the expression of POU6F2 was significantly higher in the adult-derived corneal endothelium (FIG. 8). This suggests that POU6F2 is expressed on the functional mature corneal endothelium and is related to terminal differentiation of the corneal endothelium. Therefore, POU6F2 is considered to be useful for the quality evaluation of corneal endothelial cell products, and also useful for the production of corneal endothelial cells because it is a transcription factor.

The invention claimed is:

1. A method for producing a cell population suitable for transplantation into a cornea, the method comprising the steps of:
   (1) preparing a cell population cultured under conditions suitable for inducing differentiation into corneal endothelial cells; and
   (2) measuring the expression of POU6F2 in the cell population.

2. The method according to claim 1, wherein step (1) is a step of culturing stem cells under conditions suitable for inducing differentiation into corneal endothelial cells.

3. The method according to claim 1, wherein the method further comprises measuring the expression of at least one of LMX1B and TFAP2B.

4. A method for determining whether a cell population cultured under conditions suitable for inducing differentiation into corneal endothelial cells is suitable for transplantation into a cornea, the method comprising measuring the expression of POU6F2 in the cell population, and administering to a patient in need of the administration of corneal endothelial cells the cell population in which the expression of POU6F2 has been confirmed.

5. The method according to claim 4, wherein the cell population is a cell population of stem cells cultured under conditions suitable for inducing differentiation into corneal endothelial cells.

6. The method according to claim 4, wherein the method further comprises measuring the expression of at least one of LMX1B and TFAP2B.

7. A method for producing a cell population suitable for transplantation into a cornea, the method comprising the steps of:

(1) preparing a cell population cultured under conditions suitable for culturing corneal endothelial cells; and
(2) measuring the expression of POU6F2 in the cell population.

8. The method according to claim 7, wherein the cell population cultured under conditions suitable for culturing corneal endothelial cells comprises cells obtained from a corneal endothelium.

9. The method according to claim 7, wherein the method further comprises measuring the expression of at least one of LMX1B and TFAP2B.

10. A method for determining whether a cell population cultured under conditions suitable for culturing corneal endothelial cells is suitable for transplantation into a cornea, the method comprising measuring the expression of POU6F2 in the cell population, and administering to a patient in need of the administration of corneal endothelial cells the cell population in which the expression of POU6F2 has been confirmed.

11. The method according to claim 10, wherein the cell population cultured under conditions suitable for culturing corneal endothelial cells comprises cells obtained from a corneal endothelium.

12. The method according to claim 10, wherein the method further comprises measuring the expression of at least one of LMX1B and TFAP2B.

13. A method for producing a suspension, sheet, or sphere comprising a cell population, the method comprising the steps of:
(1) preparing a cell population cultured under conditions suitable for inducing differentiation into corneal endothelial cells;
(2) measuring the expression of POU6F2 in the cell population; and
(3) preparing a suspension, sheet, or sphere comprising the cell population that expresses POU6F2.

14. The method according to claim 13, wherein step (1) is a step of culturing stem cells under conditions suitable for inducing differentiation into corneal endothelial cells.

15. The method according to claim 13, wherein the method further comprises measuring the expression of at least one of LMX1B and TFAP2B.

16. A method for producing a suspension, sheet, or sphere comprising a cell population, the method comprising the steps of:
(1) preparing a cell population cultured under conditions suitable for culturing corneal endothelial cells;
(2) measuring the expression of POU6F2 in the cell population; and
(3) preparing a suspension, sheet, or sphere comprising the cell population that expresses POU6F2.

17. The method according to claim 16, wherein the cell population cultured under conditions suitable for culturing corneal endothelial cells comprises cells obtained from a corneal endothelium.

18. The method according to claim 16, wherein the method further comprises measuring the expression of at least one of LMX1B and TFAP2B.

* * * * *